United States Patent [19]

Tabata et al.

[11] Patent Number: 4,510,341

[45] Date of Patent: Apr. 9, 1985

[54] PROCESS FOR PRODUCING CHLOROPRENE

[75] Inventors: Itsuo Tabata; Seiichi Watanabe, both of Ohmi, Japan

[73] Assignee: Denki Kagaku Kogyo Kabushiki Kaisha, Tokyo, Japan

[21] Appl. No.: 147,524

[22] Filed: May 7, 1980

[30] Foreign Application Priority Data

Jun. 4, 1979 [JP] Japan .................................. 54-69724

[51] Int. Cl.³ .............................................. C07C 17/34
[52] U.S. Cl. .................................................... 570/229
[58] Field of Search .......................... 260/655, 654 D; 570/229, 226

[56] References Cited

U.S. PATENT DOCUMENTS

| | | | |
|---|---|---|---|
| 2,322,258 | 6/1943 | Strosacker et al. | 570/229 |
| 3,079,446 | 2/1963 | MacFarlane | 570/229 |
| 3,896,181 | 7/1975 | Brown et al. | 260/655 |
| 3,936,508 | 2/1976 | Wenzel et al. | 260/655 |
| 3,965,203 | 6/1976 | Smith | 260/655 |
| 4,053,380 | 10/1977 | Fujita et al. | 260/655 |
| 4,104,316 | 8/1978 | Scharfe et al. | 260/655 |

FOREIGN PATENT DOCUMENTS 630248 10/1949 United Kingdom ............... 570/226

Primary Examiner—Charles F. Warren
Assistant Examiner—Joseph A. Boska
Attorney, Agent, or Firm—Oblon, Fisher, Spivak, McClelland & Maier

[57] ABSTRACT

Chloroprene is produced by a dehydrochlorination of 3,4-dichlorobutene-1 by contacting 3,4-dichlorobutene with a metal alkoxide of tetrahydrofurfuryl alcohol. The reaction mixture in a form of a slurry obtained by the dehydrochlorination is distilled to separate lower boiling components comprising chloroprene and the unreacted 3,4-dichlorobutene-1 as main components from higher boiling components comprising tetrahydrofurfuryl alcohol and a metal chloride as main components.

8 Claims, 1 Drawing Figure

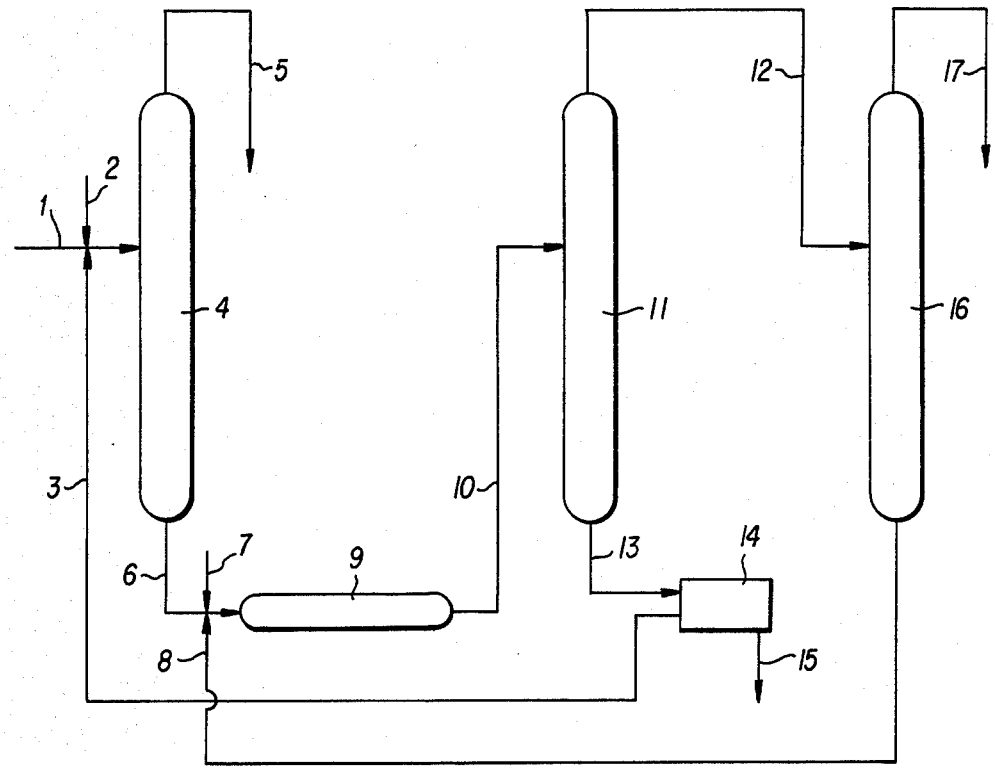

PROCESS FOR PRODUCING CHLOROPRENE

BACKGROUND OF THE INVENTION

1. Field of the Invention

The present invention relates to a process for producing chloroprene. More particularly, it relates to a process for producing chloroprene by a dehydrochlorination of 3,4-dichlorobutene-1, by contacting it with a metal alkoxide of tetrahydrofurfuryl alcohol.

2. Description of the Prior Arts

It has been known to use an aqueous solution of an alkali metal hydroxide in a dehydrochlorination of 3,4-dichlorobutene-1. In accordance with the conventional process, the reaction temperature is too high whereby the production of the by-product of 1-chlorobutadiene-1,3 is increased and chloroprene is easily polymerized. The by-production of 1-chlorobutadiene-1,3 causes a decrease of the yield of chloroprene and also a deterioration of physical property of the chloroprene polymer obtained therefrom if 1-chlorobutadiene-1,3 separated before the polymerization.

It has been proposed, as an improved process, to add an alcohol to the aqueous solution of an alkali metal hydroxide to increase the reaction velocity and to decrease the by-production of 1-chlorobutadiene-1,3 as disclosed in Japanese Unexamined Patent Publication No. 116,306/1978 and No. 106,907/1975 and Japanese Examined Patent Publication No. 11,406/1972.

It has been also proposed to provide various processes for dehydrochlorination of 3,4-dichlorobutene-1 with a metal alkoxide in a non-aqueous system as disclosed in Japanese Examined Patent Publication No. 44921/1976, Japanese Unexamined Patent Publication No. 86403/1976 and U.S. Pat. No. 3,936,508, No. 3,896,181 and No. 4,104,316.

The alcohols used in these processes include methanol, ethanol, isopropanol, n-butanol, sec-butanol, tert-butanol and 2-butoxyethanol. These are chain compounds which are azeotropically distilled with water and accordingly, the alcohol should be separated from the aqueous phase.

SUMMARY OF THE INVENTION

It is an object of the present invention to produce chloroprene at high yield under decreasing a by-production of 1-chlorobutadiene-1,3 and a polymerization of chloroprene.

It is another object of the present invention to produce chloroprene at high yield under decreasing a by-production of 1-chlorobutadiene-1,3 and a polymerization of chloroprene with an improvement of a recovery of tetrahydrofurfuryl alcohol and a recovery of a by-product salt in an advantageous process from the viewpoint of heat energy.

The other object of the present invention is to provide an improved process for utilizing a reaction heat as a heat energy for a distillation by directly feeding a reaction product in a slurry form into a distillation tower.

The foregoing and other objects of the present invention have been attained by producing chloroprene at high yield by contacting 3,4-dichlorobutene-1 with a metal alkoxide of tetrahydrofurfuryl alcohol under decreasing a by-production of 1-chlorobutadiene-1,3 and also decreasing a polymerization of chloroprene.

The further improvement of the present invention is to produce chloroprene by contacting 3,4-dichlorobutene-1 with a metal alkoxide of tetrahydrofurfuryl alcohol to carry out a dehydrochlorination and distilling the reaction mixture in a form of the slurry to separate it into higher boiling components comprising tetrahydrofurfuryl alcohol and a metal chloride as main components and lower boiling components comprising chloroprene and the unreacted 3,4-dichlorobutene-1 as the main components; if necessary under a reduced pressure and then, distilling chloroprene to separate from 3,4-dichlorobutene-1.

BRIEF DESCRIPTION OF THE DRAWING

FIGURE is a flow diagram of one embodiment of a system for the process of the present invention.

DETAILED DESCRIPTION OF THE PREFERRED EMBODIMENTS

The reaction mixture obtained by contacting 3,4-dichlorobutene-1 with the metal alkoxide of tetrahydrofurfuryl alcohol to carry out the dehydrochlorination of 3,4-dichlorobutene-1, is in the slurry form. It is not easy to filtrate the reaction mixture because chloroprene is easily polymerized. Moreover, heat energy is lost during the filtration to cause various troubles in the separation of chloroprene from the reaction mixture.

In accordance with the process of the present invention, the reaction mixture is directly distilled to separate the lower boiling components comprising chloroprene and the unreacted 3,4-dichlorobutene-1 as the main components from the higher boiling components comprising tetrahydrofurfuryl alcohol and the metal chloride, if necessary under a reduced pressure, and then, distilling chloroprene to separate from 3,4-dichlorobutene-1.

The alcohol for forming the metal alkoxide used in the process of the present invention is tetrahydrofurfuryl alcohol (hereinafter referring to as THFOH) which is the five member ring compound having one oxygen atom in the ring which has the formula

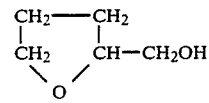

THFOH is not azeotropically distilled with water even though it is distilled in an aqueous system and impart high reaction velocity even at a relatively low temperature so as to perform the reaction as desired even in an aqueous system.

The metal alkoxide of THFOH used in the process of the present invention is a solid and can be used as an agent for dehydrochlorination of 3,4-dichlorobutene-1 in the solid form. Thus, it is not easy to use it in the solid form, whereby it is usually used in a form of a solution of THFOH.

In the production of the metal alkoxide of THFOH, THFOH and an aqueous solution of the alkali metal hydroxide are charged in a distillation tower to distil them under a dehydration, whereby water which does not substantially contain THFOH is distilled out from the top and the metal alkoxide of THFOH is obtained from the bottom.

The metal alkoxide of THFOH can be substantially the anhydrous one. Thus, even though about 10 wt.% of water is incorporated in the solution of metal alkoxide of THFOH in the process of the present invention, the reaction velocity and the production of the by-production are not substantially affected.

A concentration of the metal alkoxide of THFOH is usually higher than 10 wt.% preferably in a range of 15 to 30 wt.% especially 20 to 25 wt.%. When the concentration is higher, it is in a solid form whereas when it is lower, the amount of THFOH for recycling in the system is too large and to be uneconomical.

A reactor for the dehydrochlorination is preferably a column type reactor or a combination of a column type reactor and a vessel type reactor.

When only the vessel type reactor is used, the reaction temperature is not easily controlled because of high exothermic reaction.

A molar ratio of the metal alkoxide of THFOH to 3,4-dichlorobutene-1 is preferably higher than 0.5 especially in a range of 0.8 to 1.2. When it is lower than the stoichiometric amount, the unreacted 3,4-dichlorobutene-1 is recovered and returned to the reactor. The reaction temperature is usually in a range of 0° to 80° C. preferably 20° to 50° C.

The reaction can satisfactorily perform at lower temperature though a cost for a cooling medium is expensive. When the temperature is too high, the by-production of 1-chlorobutadiene-1,3 is increased and the polymerization of chloroprene occurs easily.

The reaction can perform under a condition of either an elevated pressure or a reduced pressure, though it is preferably in the atmospheric pressure or a reduced pressure.

A residence time is preferably shorter than 30 minutes. It is surprisingly to give high conversion such as about 90% even though it is only about one minute.

A polymerization inhibitor for chloroprene can be phenothiazine, t-butyl catechol, hydroquinone etc.

Even though a water content is about 20 wt.% in the dehydrochlorination, the conversion can be higher than 80%. When a water content is less than about 10 wt.%, the conversion can be the same as that of the reaction in the non-aqueous condition. Thus, a water content is preferably less than 30% so as to form a metal alkoxide of THFOH.

THFOH is a five member ring compound having one oxygen atom in the ring which has the structure different from the alcohols for the known alkoxides as the agents for the dehydrochlorination of 3,4-dichlorobutene-1.

THFOH has the characteristic which is not azeotropically distilled with water, whereby a recovery ratio of the alcohol is high and the process is simplified. Moreover, the reaction velocity is high enough to perform the reaction at a relatively low temperature. The reaction is not limited to a non-aqueous condition to give at high conversion as that of the reaction in the non-aqueous system.

The characteristic feature of the present invention is as follows. A reaction mixture in a slurry form obtained by the dehydrochlorination of 3,4-dichlorobutene-1 by contacting it with the metal alkoxide of THFOH, is fed into a distillation tower to distil chloroprene and the unreacted 3,4-dichlorobutene-1 and then, the bottom residue is treated by a mechanical manner such as a centrifugal separation to separate the metal chloride and the resulting THFOH is recovered and reused. On the other hand, the mixture of chloroprene and the unreacted 3,4-dichlorobutene-1 is fed into the next distillation tower, if necessary without substantially cooling it to separate chloroprene by a distillation. Therefore, the reaction heat in the reactor can be utilized for the distillation of the mixture of chloroprene and the unreacted 3,4-dichlorobutene-1 to provide the remarkable advantage from the viewpoint of heat energy.

The distillation of the reaction mixture in a slurry form is preferably carried out under a reduced pressure. The preferable condition in the distillation is as follows.

A concentration of chloroprene in the reaction mixture in a slurry form is in a range of 5 to 20 wt.% preferably 10 to 15 wt.%. A concentration of tetrahydrofurfuryl alcohol is in a range of 60 to 80 wt.% preferably 65 to 75 wt.%.

It preferably minimize a temperature falling in the step of transferring the reaction mixture from the reactor to the distillation tower.

The temperature for the distillation of the reaction mixture in the slurry form is depending upon the degree of the reduced pressure and should be the temperature for distilling chloroprene and the unreacted 3,4-dichlorobutene-1.

One embodiment for the production of chloroprene by using sodium alkoxide of THFOH as the metal alkoxide of THFOH will be illustrated referring to the drawing.

Into a first distillation tower (4), an aqueous solution of sodium hydroxide is fed through a line (1) and THFOH is fed through a line (2) and a recycling THFOH is fed through a line (3) in the continuous condition.

The first distillation tower (4) can be any pressure condition, i.e. an elevated pressure, the atmospheric pressure or a reduced pressure. When it is operated under a reduced pressure, a decomposition of THFOH is advantageously small and a formation of the metal alkoxide is advantageously large. The concentration of the aqueous solution of sodium hydroxide is not critical and is preferably to be relatively higher so as to decrease a quantity of the distilled water. The rates for feeding these components are selected depending upon the reaction condition and the distillation rate from the reaction mixture in the slurry form. THFOH is not azeotropically distilled with water whereby only water which does not substantially contain THFOH is distilled from the top and is discharged through the line (5). The solution of sodium alkoxide of THFOH is discharged through the line (6) of the bottom.

A concentration of the alkoxide in THFOH is usually higher than 10 wt.% preferably in a range of 15 to 30 wt.% especially 20 to 25 wt.%. When the concentration is too high, the solid alkoxide is formed, whereas when it is lower, a quantity of the recycling THFOH in the system is too much. This is not economical.

In the reactor (9) for the dehydrochlorination, 3,4-dichlorobutene-1 fed through the line (7) and the recycling 3,4-dichlorobutene-1 fed through the line (8) react with the solution of sodium alkoxide in THFOH fed through the line (6).

A reaction temperature is preferably in a range of 0° to 80° C. especially 20° to 50° C. A molar ratio of the metal alkoxide of THFOH to 3,4-dichlorobutene-1 is usually higher than 0.5 preferably in a range of 0.8 to 1.2 especially 0.8 to 1.0.

It is preferable to substantially react the metal alkoxide in the step of the recovery of THFOH by the distillation from the sodium chloride mixture separated by a separator because of high recovery percent of THFOH.

The pressure in the reactor is preferably the atmospheric pressure or a reduced pressure because it is preferable to directly transfer the reaction mixture in the slurry form into the second distillation tower and to distil it under a reduced pressure in the second distillation tower.

The residence time is preferably shorter than 30 minutes and is selected depending upon the reaction condition.

It is possible to add a polymerization inhibitor for chloroprene such as phenothiazine, t-butyl catechol, hydroquinone etc.

The type of the reactor is preferably a column type reactor which has high heat removing effect. It is also preferable to use a combination of the column type reactor and a vessel type reactor. It is also possible to simultaneously carry out the reaction and the distillation of the reaction mixture in the slurry form resulted by the reaction, in the second distillation tower (11) without employing the reactor (9).

The reaction mixture in the reactor (9) in the slurry form is fed through the line (10) into a second distillation tower (11). The second distillation tower (11) can be operated under the atmospheric pressure or a reduced pressure. It is preferable to be a reduced pressure so as to prevent the polymerization of chloroprene. Chloroprene and the unreacted 3,4-dichlorobutene-1 are distilled out from the top. When water is remained in the solution of the metal alkoxide, water is distilled off from the top. Water can be discharged out of the system by an equipment of a decanter in the line (12). THFOH and sodium chloride are discharged from the bottom and are fed through the line (13) into the separator (14).

A centrifugal separator or a filter-press, etc. can be used as a separator. A filtrate is recycled through the line (3) into the first distillation tower (4). A concentration of sodium chloride in the filtrate is preferably lower. It is possible to recycle the solution containing sodium chloride at a concentration of upto about 5 wt.% into the first distillation tower (4). Most of sodium chloride is discharged through the line (15) out of the system. THFOH in the sodium chloride mixture can be recovered by a distillation if necessary.

The components of the reaction mixture in the slurry form fed in the second distillation tower are given depending upon the ratios of the components in the reactor. Therefore, they are given under the above-mentioned feeding condition.

Chloroprene and the unreacted 3,4-dichlorobutene-1 are fed through the line (12) into a third distillation tower (16). Chloroprene is distilled out from the top and discharged through a line (17) out of the system whereas 3,4-dichlorobutene-1 is recovered from the bottom and is recycled through the line (8) into the reactor (9).

It is possible to discharge a part of the reaction mixture through the line (3) and to recover THFOH by its distillation and to recycle THFOH so as to eliminate higher boiling impurities accumulated in the system.

In the second and third distillation towers, it is possible to add an effective amount of a polymerization inhibitor for preventing the polymerization of chloroprene.

In accordance with the process of the present invention, the unreacted 3,4-dichlorobutene-1 can be utilized without a loss and sodium hydroxide and THFOH can be also effectively used without a substantial loss. Moreover, the reaction heat generated in the reactor can be utilized, without a substantial loss, for the distillation in the second distillation tower. Sodium chloride can be mechanically separated from THFOH. The energy for the separation can be remarkably small. THFOH can be recycled without a purification.

The embodiment using sodium alkoxide of THFOH is illustrated. The same operation can be carried out by using the other metal alkoxide such as potassium alkoxide instead of sodium alkoxide.

In the drawing, THFOH is fed through the line (3) and 3,4-dichlorobutene-1 is fed through the line (8) in the recycling. In the process of the present invention, it is not limited to such recycling. THFOH can be fed after the first distillation tower or 3,4-dichlorobutene-1 can be directly fed into the second distillation tower without employing the reactor. Various modifications can be applied.

The present invention will be further illustrated by certain example which is provided for purposes of illustration only and are not intended to be limiting the present invention. In the example, the term of part means a part by weight.

EXAMPLE 1

In the system shown by the flow diagram, 156 wt. parts of 30% aqueous solution of sodium hydroxide, 6 wt. parts of sodium chloride and 559 wt. parts of THFOH solution including a filtrate obtained by a centrifugal separator were respectively fed into the first distillation tower (4) which was a tower packed with Raschig's rings and operated under a reduced pressure of 100 Torr and had a temperature of about 48° C. at the top and about 125° C. at the bottom. A capacity of the heater was 2 liters and a residence time was 2.5 hours. From the top, 128 wt. parts of water which did not substantially contain THFOH was distilled off to be discharged out of the system. From the bottom, 587 wt. parts of a solution containing 145 wt. parts of sodium alkoxide of THFOH and sodium chloride in THFOH was discharged. In the solution, about 0.4 wt. % of water was contained.

The solution of sodium alkoxide of THFOH, 18 wt. parts of 3,4-dichlorobutene-1 containing a samll amount of chloroprene obtained from the bottom of the third distillation tower (16) and 146 wt. parts of 3,4-dichlorobutene-1 were fed into the reactor (9) which was a jacket had an inner diameter of 17.8 mm and a length of 500 mm and made of stainless steel. The temperature at the outlet was controlled to 40° C. The pressure was the atmospheric pressure. A molar ratio of sodium alkoxide of THFOH to 3,4-dichlorobutene-1 was 0.9 and a residence time was 5 minutes. The conversion was substantially 100% based on the sodium alkoxide of THFOH. The unreacted sodium alkoxide of THFOH was not substantially found.

The reaction product was fed into the second distillation tower (11) in a form of a slurry. The distillation tower (11) was operated under a reduced pressure of 130 Torr. The temperature was about 30° C. at the top and about 120° C. at the bottom. A heater was a 2 liter vessel equipped with a stirrer. From the top, 123 wt. parts of a lower boiling solution containing 105 wt. parts of chloroprene and 3,4-dichlorobutene-1 was distilled out. Water was separated by a decanter, and the chloroprene solution as the upper phase was fed into the third distillation tower (16). On the other hand, 627 wt. parts of THFOH solution containing 74 wt. parts of sodium chloride was fed into a centrifugal separator to obtain 556 wt. parts of a filtrate. The filtrate which contained about 1.1% of sodium chloride was recycled to the first distillation tower. About 4% of THFOH was included in 71 wt. parts of solid sodium chloride. In the example, THFOH was not recovered by an evaporation.

Into the third distillation tower, the lower boiling solution containing 105 wt. parts of chloroprene obtained from the second distillation tower was fed. The tower was operated under a reduced pressure of 130 Torr to distil off 102 wt. parts of chloroprene from the top and to discharge 18 wt. parts of 3,4-dichlorobutene-1 containing a small amount of chloroprene from the bottom which was recycled to the reactor (9).

The purity of chloroprene was higher than 99% and the yield was about 98%. The loss of THFOH was about 3 kg. per 100 kg. of the production of chloroprene.

EXAMPLES 2 TO 6

A 2 liter four necked flask was connected to a distillation tower packed with Raschig's rings. In the flask, 1,800 ml. of THFOH and 50% aqueous solution of 160 g. of sodium hydroxide were charged and dehydrated and distilled under a reduced pressure of 100 Torr. The temperature was 92° C. at the bottom and 52° C. at the top. Water distilled from the top did not substantially contain THFOH. A water content in sodium alkoxide was less than 0.3 wt.%.

A reactor for a dehydrochlorination was a column type reactor equipped with a jacket having an inner diameter of 0.98 cm and a length of 65 cm. Thermometers were equipped at several parts of the reactor to control the temperature at the outlet of the reactor as the reaction temperature. A molar ratio of sodium alkoxide to 3,4-dichlorobutene-1 was controlled to 1.2. The components were fed continuously into the reactor at rates depending upon each residence time. When the operation was in the normal state, a part of the discharged mixture from the reactor was sampled into an aqueous solution of hydrochloric acid to stop the reaction and analyzed by a gas chromatography. The result is shown in Table 1. The by-product of sodium chloride was in a solid condition.

EXAMPLES 7 TO 8

In accordance with the process of Examples 2 to 6, each dehydrochlorination was carried out by adding water at each ratio shown in Table 1 to the alkoxide.

EXAMPLES 9 TO 10

In accordance with the process of Examples 2 to 6, except using potassium hydroxide instead of sodium hydroxide and adding 225 g. of potassium hydroxide into 1800 ml. of THFOH and dehydrating and distilling under a reduced pressure of 100 Torr, each dehydrochlorination was carried out.

REFERENCES 1 TO 5 AND REFERENCES 8 TO 9

In accordance with the process of Examples 2 to 6 except that a solvent corresponding to the distilled solvent measured by a gas chromatography (water and the solvent are distilled from the top of the distillation tower in the production of the alkoxide) is added to the alkoxide, each dehydrochlorination was carried out.

REFERENCES 6 AND 10

In accordance with the process of References 1 to 5 and 8 to 9, water was added to the alkoxide at a ratio shown in Table 2, each dehydrochlorination was carried out.

REFERENCES 7 AND 11

In accordance with the process of Examples 9 and 10 using potassium hydroxide except adding a solvent corresponding to the solvent distilled from the top, to the alkoxide, each dehydrochlorination was carried out.

In Tables 1 and 2, the term 1-CP means 1-chlorobutadiene-1,3.

TABLE 1

| | Example | | | | | | | | |
|---|---|---|---|---|---|---|---|---|---|
| | 1 | 2 | 3 | 4 | 5 | 6 | 7 | 8 | 9 |
| Alkoxide | Na alkoxide of THFOH | | | | | | | K alkoxide of THFOH | |
| Solvent | THFOH | | | | | | | THFOH | |
| Concentration (wt. %) | | | | | | | | | |
| Alkoxide | 24.9 | 24.9 | 24.9 | 24.8 | 24.9 | 22.2 | 18.6 | 27.0 | 27.2 |
| Water | 0.1 | 0.1 | 0.1 | 0.3 | 0.1 | 10.8 | 25.5 | 0.1 | 0.1 |
| Reaction temp. (°C.) | 40 | 40 | 40 | 20 | 20 | 40 | 40 | 40 | 40 |
| Residence time (min.) | 10 | 2.5 | 1 | 10 | 2.5 | 2.5 | 2.5 | 10 | 1 |
| Conversion (%) | 94.6 | 94.1 | 88.8 | 93.6 | 83.0 | 93.4 | 85.4 | 80.3 | 83.5 |
| 1-CP by product percent (%) | 0.38 | 0.32 | 0.34 | 0.28 | 0.25 | 0.40 | 0.35 | 0.43 | 0.39 |

TABLE 2

| | Reference | | | | | | | | | | |
|---|---|---|---|---|---|---|---|---|---|---|---|
| | 1 | 2 | 3 | 4 | 5 | 6 | 7 | 8 | 9 | 10 | 11 |
| Alkoxide | Na—Bu | | | | | | K—Bu | Na—Bu.Et | | | K—Bu.Et |
| Solvent | n-butanol | | | | | | n-butanol | 2-butoxyethanol | | | 2-butoxyethanol |
| Concentration (wt. %) | | | | | | | | | | | |
| Alkoxide | 24.5 | 24.8 | 24.5 | 24.1 | 24.8 | 22.4 | 27.0 | 33.1 | 32.1 | 29.9 | 35.3 |
| Water | 0.3 | 0.5 | 0.3 | 0.5 | 0.5 | 11.1 | 0.4 | 0.1 | 0 | 10.3 | 0.3 |
| Reaction temp. (°C.) | 40 | 40 | 40 | 20 | 20 | 40 | 40 | 40 | 40 | 40 | 40 |

TABLE 2-continued

|  | Reference | | | | | | | | | | |
| --- | --- | --- | --- | --- | --- | --- | --- | --- | --- | --- | --- |
|  | 1 | 2 | 3 | 4 | 5 | 6 | 7 | 8 | 9 | 10 | 11 |
| Residence time (min.) | 10 | 2.5 | 1 | 10 | 2.5 | 2.5 | 1 | 10 | 2.5 | 2.5 | 1 |
| Conversion (%) | 79.2 | 75.1 | 64.4 | 67.6 | 59.5 | 55.1 | 71.0 | 79.1 | 72.2 | 72.7 | 75.0 |
| 1-CP by product percent (%) | 0.47 | 0.37 | 0.37 | 0.32 | 0.33 | 0.41 | 0.40 | 0.39 | 0.38 | 0.43 | 0.40 |

Note:
Na—Bu: Na butoxide
K—Bu: K butoxide
Na—Bu.Et: Na 2-butoxyethoxide
K—Bu.Et: K 2-butoxyethoxide

We claim:

1. A process for producing chloroprene which comprises a dehydrochlorination of 3,4-dichlorobutene-1 by contacting 3,4-dichlorobutene-1 with the sodium alkoxide of tetrahydrofurfuryl alcohol.

2. The process for producing chloroprene according to claim 1, wherein said sodium alkoxide of tetrahydrofurfuryl alcohol is used as a solution in tetrahydrofurfuryl alcohol.

3. The process for producing chloroprene according to claim 1, wherein the reaction mixture, in the form of a slurry, obtained by the dehydrochlorination is distilled to separate lower boiling components comprising chloroprene and the unreacted 3,4-dichlorobutene-1, as main components, from higher boiling components comprising tetrahydrofurfuryl alcohol and sodium chloride, as main components.

4. The process for producing chloroprene according to claim 3, wherein tetrahydrofurfuryl alcohol is recovered from the higher boiling components and is converted into the sodium alkoxide of tetrahydrofurfuryl alcohol and recycled; and the 3,4-dichlorobutene-1 remaining after separation of chloroprene from the lower boiling components is recycled.

5. The process for producing chloroprene according to claim 3, wherein the reaction mixture in slurry form is obtained by reacting the sodium alkoxide of tetrahydrofurfuryl alcohol with 3,4-dichlorobutene-1 at a molar ratio of the sodium alkoxide of tetrahydrofurfuryl alcohol to 3,4-dichlorobutene-1 higher than 0.5.

6. The process for producing chloroprene according to claim 3, 4 or 5, wherein the sodium alkoxide of tetrahydrofurfuryl alcohol, obtained by distilling a mixture of tetrahydrofurfuryl alcohol and an aqueous solution of sodium hydroxide in a first distillation tower, is contacted with 3,4-dichlorobutene-1 to react them; and the reaction mixture, in slurry form, is fed into a second distillation tower to separate lower boiling components from higher boiling components; and the lower boiling components are fed into a third distillation to distill off chloroprene and recover it.

7. The process for producing chloroprene according to claim 3, 4 or 5, wherein the distillation of the reaction mixture, in slurry form, is carried out under reduced pressure.

8. The process for producing chloroprene according to claim 6, wherein the distillation of the reaction mixture, in slurry form, is carried out under reduced pressure.

* * * * *